US011051931B2

(12) United States Patent
Swensgard et al.

(10) Patent No.: US 11,051,931 B2
(45) Date of Patent: Jul. 6, 2021

(54) ACTIVE SPHINCTER IMPLANT TO RE-ROUTE FLOW THROUGH GASTROINTESTINAL TRACT

(71) Applicants: ETHICON LLC, Guaynabo, PR (US); TORAX MEDICAL, INC., Shoreview, MN (US)

(72) Inventors: Brett E. Swensgard, West Chester, OH (US); Michael D. Auld, West Union, OH (US); Celeste L. Huster, Blaine, MN (US)

(73) Assignees: Cilag GmbH International, Zug (CH); Torax Medical, Inc., Shoreview, MN (US)

( * ) Notice: Subject to any disclaimer, the term of this patent is extended or adjusted under 35 U.S.C. 154(b) by 116 days.

(21) Appl. No.: 16/176,163

(22) Filed: Oct. 31, 2018

(65) Prior Publication Data
US 2020/0129283 A1 Apr. 30, 2020

(51) Int. Cl.
*A61F 2/04* (2013.01)

(52) U.S. Cl.
CPC .......... *A61F 2/04* (2013.01); *A61F 2002/045* (2013.01); *A61F 2210/009* (2013.01); *A61F 2250/0001* (2013.01); *A61F 2250/008* (2013.01)

(58) Field of Classification Search
CPC ............................... A61F 2/04; A61L 27/3679
USPC ........................................... 623/23.64–23.68
See application file for complete search history.

(56) References Cited

U.S. PATENT DOCUMENTS

| 5,122,136 A | 6/1992 | Guglielmi et al. |
| 5,204,382 A | 4/1993 | Wallace et al. |
| 5,509,888 A | 4/1996 | Miller |
| 5,702,361 A | 12/1997 | Evans, II et al. |
| 6,543,456 B1 | 4/2003 | Freeman |
| 7,175,589 B2 | 2/2007 | Deem et al. |

(Continued)

FOREIGN PATENT DOCUMENTS

| DE | 3011742 A1 | 10/1981 |
| EP | 1547549 A2 | 6/2005 |

(Continued)

OTHER PUBLICATIONS

U.S. Appl. No. 15/914,381, entitled "Tunable Magnetic Sphincter Augmentation Device," filed Mar. 7, 2018.

*Primary Examiner* — Suzette J Gherbi
(74) *Attorney, Agent, or Firm* — Frost Brown Todd LLC

(57) ABSTRACT

A method is provided for rerouting flow through the small intestine of a patient with an implanted artificial sphincter that encircles a portion of the small intestine. The small intestine includes a duodenum, a jejunum extending from the duodenum, and an ileum extending from the jejunum. The method includes providing the artificial sphincter in an open state to thereby permit intestinal flow through the encircled portion of the small intestine such that the intestinal flow passes through the duodenum, the jejunum, and the ileum. The method further includes, in response to a user-activated electrical input, transitioning the artificial sphincter to a closed state to constrict the encircled portion of the small intestine and thereby redirect intestinal flow from a first portion of the small intestine to a second portion of the small intestine such that the intestinal flow bypasses at least a portion of the jejunum.

20 Claims, 7 Drawing Sheets

(56) References Cited

U.S. PATENT DOCUMENTS

| | | |
|---|---|---|
| 7,191,007 B2 | 3/2007 | Desai et al. |
| 7,351,240 B2 | 4/2008 | Hassler, Jr. et al. |
| 7,374,565 B2 | 5/2008 | Hassler, Jr. et al. |
| 7,390,294 B2 | 6/2008 | Hassler, Jr. |
| 7,445,010 B2 | 11/2008 | Kugler et al. |
| 7,481,763 B2 | 1/2009 | Hassler, Jr. et al. |
| 7,599,743 B2 | 10/2009 | Hassler, Jr. et al. |
| 7,599,744 B2 | 10/2009 | Giordano et al. |
| 7,695,427 B2 | 4/2010 | Kugler et al. |
| 7,727,141 B2 | 6/2010 | Hassler, Jr. et al. |
| 7,879,068 B2 | 2/2011 | Dlugos et al. |
| 8,070,670 B2 | 12/2011 | Deem et al. |
| 8,603,023 B2 | 12/2013 | Albrecht et al. |
| 8,617,049 B2 | 12/2013 | Dlugos, Jr. et al. |
| 8,636,751 B2 | 1/2014 | Albrecht et al. |
| 8,715,157 B2 | 5/2014 | Berg et al. |
| 8,734,475 B2 | 5/2014 | Ekvall et al. |
| 8,870,742 B2 | 10/2014 | Dlugos, Jr. et al. |
| 8,876,761 B2 | 11/2014 | Albrecht et al. |
| 9,814,561 B2 * | 11/2017 | Forsell ................ A61M 1/1041 |
| 2005/0256587 A1 * | 11/2005 | Egan ........................ A61F 2/04 |
| | | 623/23.65 |
| 2005/0283235 A1 | 12/2005 | Kugler et al. |
| 2005/0288739 A1 | 12/2005 | Hassler et al. |
| 2007/0010866 A1 * | 1/2007 | Dann .................... A61F 5/0086 |
| | | 623/1.11 |
| 2009/0062824 A1 | 3/2009 | Berg et al. |
| 2011/0087337 A1 * | 4/2011 | Forsell .................. A61B 17/12 |
| | | 623/23.68 |
| 2011/0098731 A1 | 4/2011 | Whitbrook et al. |
| 2013/0013084 A1 * | 1/2013 | Birk ...................... A61F 5/0079 |
| | | 623/23.68 |
| 2015/0209173 A1 * | 7/2015 | Kratky .................... A61F 5/445 |
| | | 604/337 |
| 2018/0235794 A1 * | 8/2018 | Kagan ........................ A61F 2/04 |
| 2018/0243074 A1 * | 8/2018 | Forsell ................ A61M 1/1041 |
| 2019/0029689 A1 | 1/2019 | Shelton, IV et al. |

FOREIGN PATENT DOCUMENTS

| | | |
|---|---|---|
| WO | WO 1993/015721 A1 | 8/1993 |
| WO | WO 1993/016658 A1 | 9/1993 |
| WO | WO 1993/019702 A1 | 10/1993 |
| WO | WO 1997/033632 A2 | 9/1997 |
| WO | WO 1998/044965 A1 | 10/1998 |
| WO | WO 2000/054835 A1 | 9/2000 |
| WO | WO 2001/047431 A2 | 4/2001 |

* cited by examiner

ACTIVE SPHINCTER IMPLANT TO RE-ROUTE FLOW THROUGH GASTROINTESTINAL TRACT

BACKGROUND

In some instances, it may be desirable to place a medical implant within or surrounding an anatomical passage in order to improve or assist the function of, or otherwise affect, the anatomical passage. Examples of such anatomical passages include, but are not limited to, an esophagus, a fallopian tube, a urethra, or a blood vessel. Some anatomical passages normally function by expanding and contracting actively or passively to regulate the flow of solids, liquids, gasses, or a combination thereof. The ability of an anatomical passage to expand and contract may be compromised by defects or disease. One merely illustrative example of a condition associated with decreased functionality of an anatomical passage is Gastro Esophageal Reflux Disease ("GERD"), which effects the esophagus.

Implantable artificial sphincters have been used in various medical applications to affect the function of anatomical passages. Examples of artificial sphincters and related methods that provide augmentation of natural sphincters are disclosed in U.S. Pat. No. 7,175,589, entitled "Methods and Devices for Luminal and Sphincter Augmentation," issued Feb. 13, 2007; U.S. Pat. No. 7,695,427, entitled "Methods and Apparatus for Treating Body Tissue Sphincters and the Like," issued Apr. 13, 2010; U.S. Pat. No. 8,070,670, entitled "Methods and Devices for Luminal and Sphincter Augmentation," issued Dec. 6, 2011; U.S. Pat. No. 8,715,157, entitled "Magnetic Gastric Band or the Like, and Related Methods," issued May 6, 2014; and U.S. Pat. No. 8,734,475, entitled "Medical Implant with Floating Magnets," issued May 27, 2014. The disclosure of each of these references is incorporated by reference herein.

In various applications, it may be desirable to wirelessly transfer electrical energy to an implanted artificial sphincter via transcutaneous energy transfer (TET), which enables the sphincter to operate without percutaneous placement of wires, instruments, or the like that might otherwise risk patient infection. Exemplary implantable devices and related methods that employ TET are disclosed in U.S. Pub. No. 2005/0288739, entitled "Medical Implant Having Closed Loop Transcutaneous Energy Transfer (TET) Power Transfer Regulation Circuitry," published Dec. 29, 2005; U.S. Pat. No. 7,191,007, entitled "Spatially Decoupled Twin Secondary Coils for Optimizing Transcutaneous Energy Transfer (TET) Power Transfer Characteristics," issued Mar. 13, 2007; U.S. Pat. No. 7,351,240, entitled "Thermodynamically Driven Reversible Infuser Pump for Use as a Remotely Controlled Gastric Band," issued Apr. 1, 2008; U.S. Pat. No. 7,374,565, entitled "Bi-Directional Infuser Pump with Volume Braking for Hydraulically Controlling an Adjustable Gastric Band," issued May 20, 2008; U.S. Pat. No. 7,390,294, entitled "Piezo Electrically Driven Bellows Infuser for Hydraulically Controlling an Adjustable Gastric Band," issued Jun. 24, 2008; U.S. Pat. No. 7,481,763, entitled "Metal Bellows Position Feedback for Hydraulic Control of an Adjustable Gastric Band," issued Jan. 27, 2009; European Pat. No. 1547549, entitled "Mechanically Adjustable Gastric Band," issued Aug. 26, 2009; U.S. Pat. No. 7,599,743, entitled "Low Frequency Transcutaneous Energy Transfer to Implanted Medical Device," issued Oct. 6, 2009; U.S. Pat. No. 7,727,141, entitled "Magnetic Resonance Imaging (MRI) Safe Remotely Adjustable Artificial Sphincter," issued Jun. 1, 2010; U.S. Pat. No. 7,599,744, entitled "Transcutaneous Energy Transfer Primary Coil with a High Aspect Ferrite Core," issued Oct. 6, 2010; U.S. Pat. No. 7,879,068, entitled "Feedback Sensing for a Mechanical Restrictive Device," issued Feb. 1, 2011; and U.S. Pat. No. 8,870,742, entitled "GUI for an Implantable Restriction Device and a Data Logger," issued Oct. 28, 2014. The disclosure of each of these references is incorporated by reference herein.

While various types of devices and methods have been employed to treat or otherwise affect anatomical passages, it is believed that no one prior to the inventors has made or used an invention as described herein.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
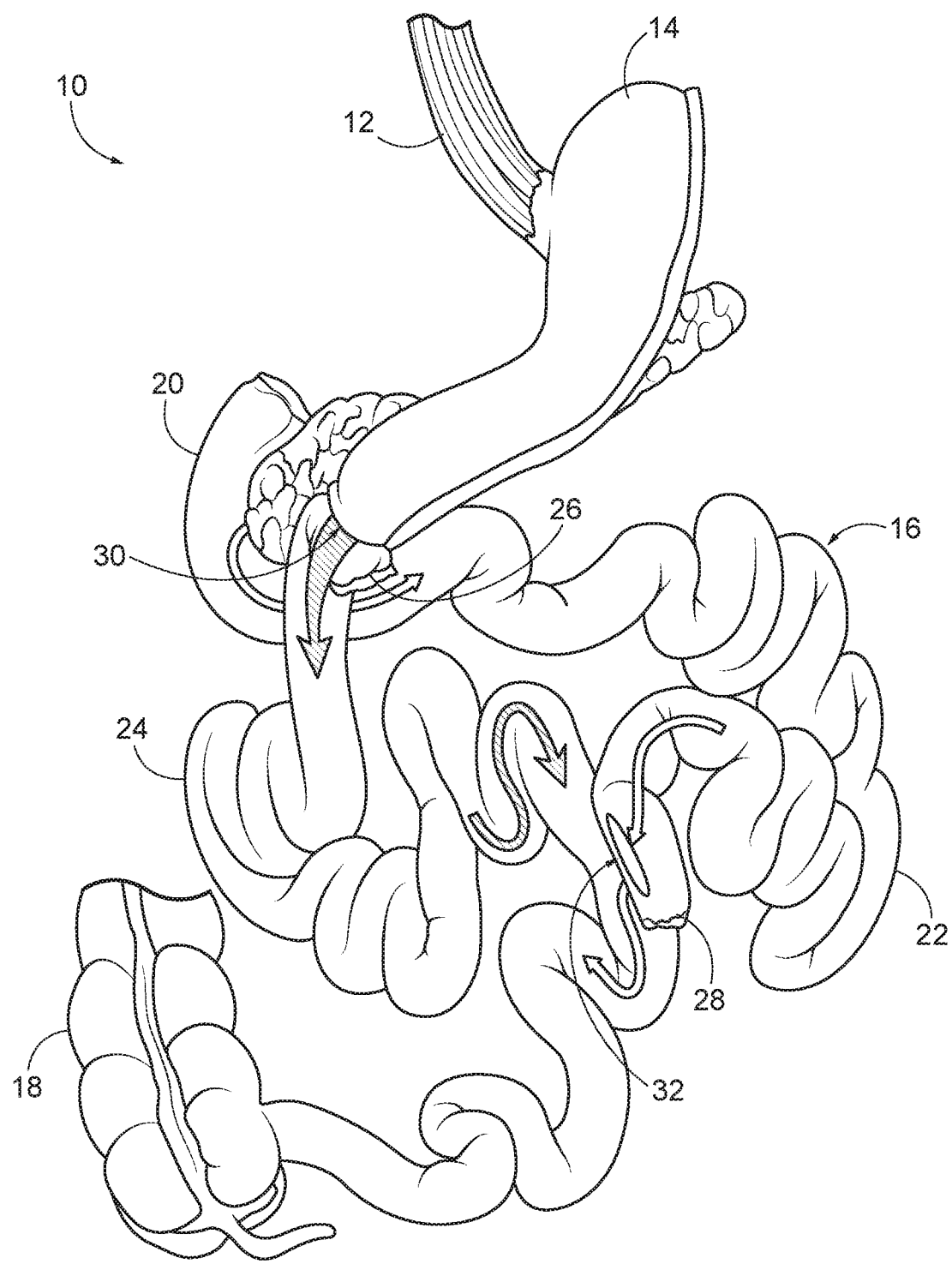
FIG. 1 depicts a schematic front view of a gastrointestinal tract of a human patient after having undergone a traditional gastric bypass procedure.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Procedure and Implant Device that Redirects Intestinal Flow in Response to User Input FIG. 1 shows a gastrointestinal tract (10) of a human patient after having undergone a "biliopancreatic diversion with duodenal switch" (BPD/DS) gastric bypass procedure. The illustrated portion of gastrointestinal tract (10) includes an esophagus (12), a stomach (14), a small intestine (16), and a large intestine (or "colon") (18). Small intestine (16) includes a duodenum (20), a jejunum (22), and an ileum (24). In its natural state, small intestine (16) is arranged such that duodenum (20) extends directly from an outlet end (or "pyloric region") of stomach (14), jejunum (22) extends from a downstream end of duodenum (20), ileum (24) extends from a downstream end of jejunum (22), and a downstream end of ileum (24) connects with an ascending portion of colon (18).

Gastrointestinal tract (10) of the present example is shown surgically reconfigured via the BPD/DS gastric procedure such that a portion of stomach (14) along its greater curvature has been removed, leaving a tubular-shaped pouch. Additionally, small intestine (16) has been surgically reconfigured such that an upstream end of duodenum (20) is separated from the outlet end of stomach (14) and is sealed closed, and a downstream portion of small intestine (16) is transected to create a first transected end (26) that communicates directly with an upstream portion of ileum (24), and a second transected end (28) that communicates directly with a downstream portion of jejunum (22). First transected end (26) is then surgically joined with the outlet end of stomach (14) via an end-to-end anastomosis (30), and second transected end (28) is surgically joined with a lower portion of ileum (24) via a side-by-side anastomosis (32). Anastomoses (30, 32) may be formed using various suitable surgical methods readily apparent to those of ordinary skill art, such as stapling and/or suturing, for example.

The partially digested food and liquids (or "chyme") that exit stomach (14) thus pass directly into the lower portion of small intestine (16) and bypass most or all of jejunum (22), depending on placement of the transection that defines first and second transected ends (26, 28). The bypassed portion of small intestine (16) delivers bile and pancreatic enzymes into the lower portion of small intestine (16), via side-by-side anastomosis (32), such that the chyme does not mix with the bile and enzymes until the chyme approaches colon (18). This surgical reconfiguration of gastrointestinal tract (10) results in a significant decrease in the absorption of calories and nutrients, particularly protein and fat, as well as nutrients and vitamins dependent on fat for absorption (e.g., fat-soluble vitamins and nutrients), thus providing the patient with an effective weight loss treatment.

The BPD/DS gastric bypass procedure described above, though generally effective as a weight loss treatment, is complex to perform and can cause various post-surgery complications for the patient. Moreover, because the procedure is entirely surgical, it is generally permanent and not reversible. In some instances, it may be desirable to provide a patient with a gastric bypass procedure of similar effectiveness but less surgically complex and also easily reversible. The exemplary procedure and implant device (100) described below provide a human patient with a gastric bypass procedure that is selectively reversible in part without surgical invasion so that the flow of chyme through small intestine (16) may be selectively transitioned between a bypass flow path and a natural flow path in response to a user input.

Figure 2A:
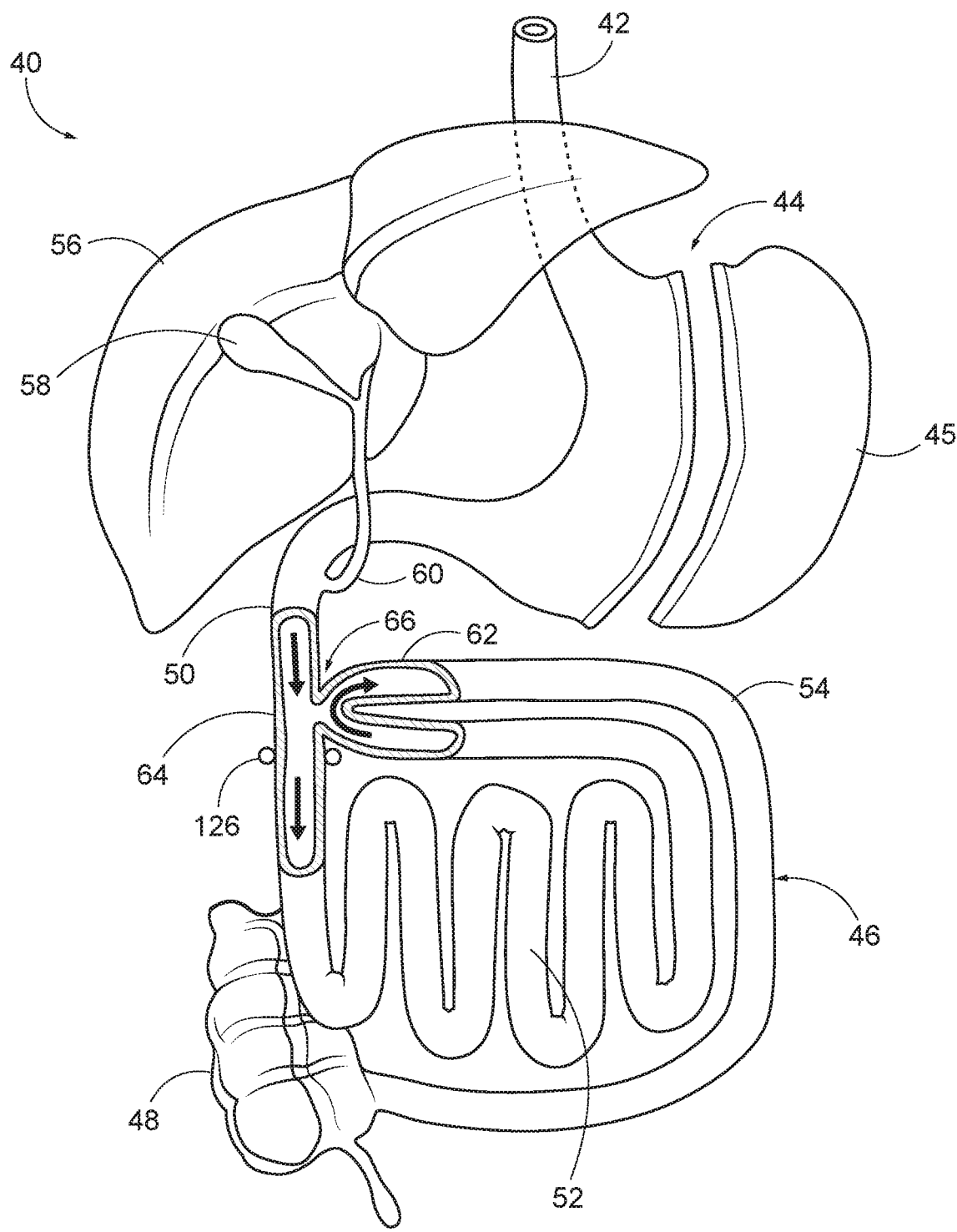
FIG. 2A depicts a schematic front view of a gastrointestinal tract of a human patient after having undergone surgical steps of an exemplary gastric procedure, showing an artificial sphincter encircling a portion of the small intestine located downstream of an anastomosis formed between the duodenum and the ileum, with the artificial sphincter in an open state that permits a traditional flow path through the small intestine.
Figure 2B:
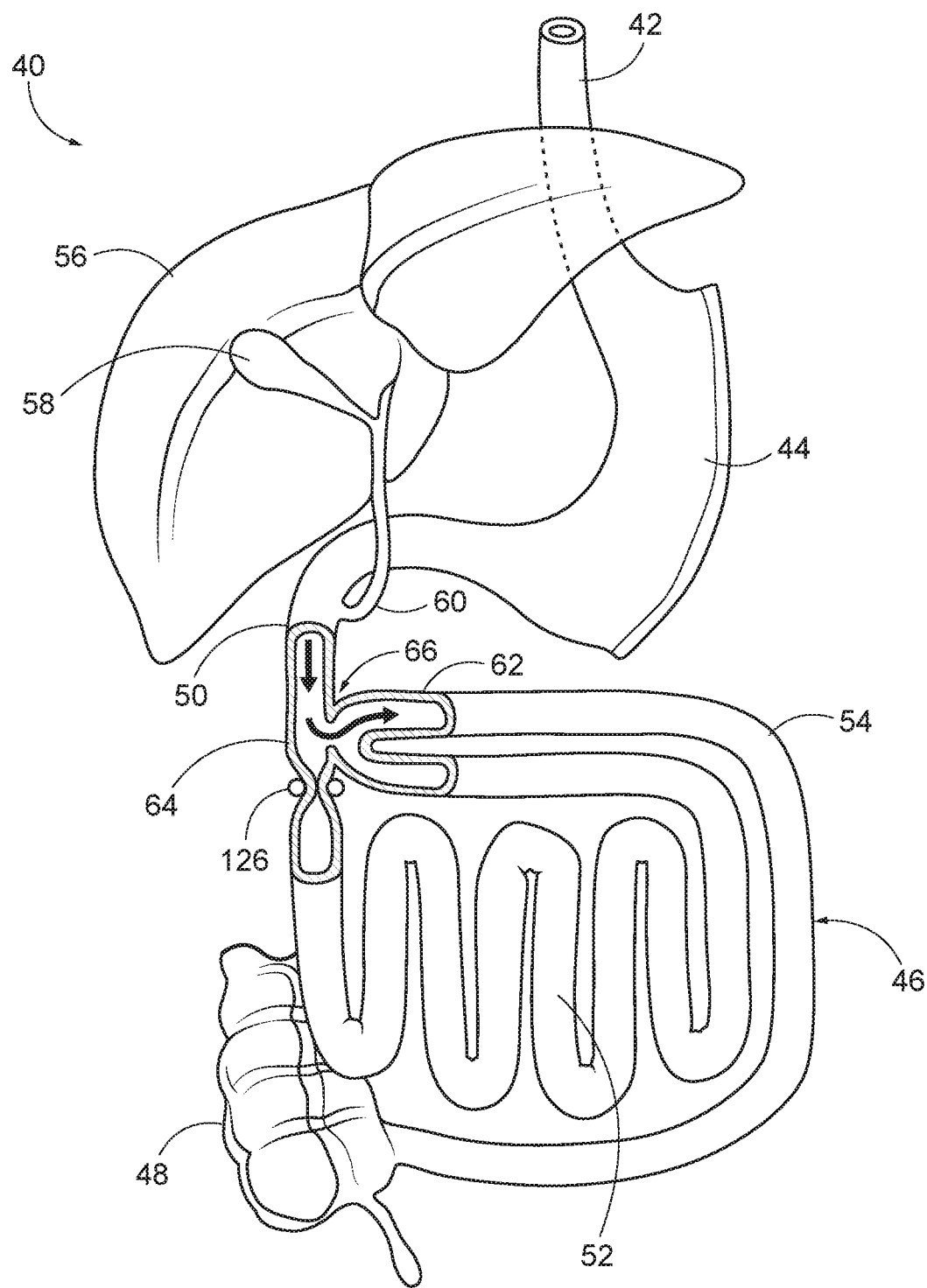
FIG. 2B depicts a schematic front view of the gastrointestinal tract of FIG. 2A, showing the artificial sphincter in a closed state that results in the intestinal flow being redirected through the anastomosis such that the intestinal flow passes directly from the duodenum to the ileum and bypasses the jejunum.

A. Overview of Exemplary Procedure that Enables Selective Redirection of Flow Through Small Intestine FIGS. 2A and 2B show a human gastrointestinal tract (40) having an esophagus (42), a stomach (44), a small intestine (46), and a colon (48). Small intestine (46) includes a duodenum (50), a jejunum (52), and an ileum (54). Also shown is a liver (56) which creates bile, and a gall bladder (58) in which the bile is stored before being directed into gastrointestinal tract (40). A common bile duct exiting from the gall bladder (58) joins with a pancreatic duct exiting from a pancreas (not shown) to define an ampulla of Vater (60) (also known as the "hepatopancreatic ampulla" or the "hepatopancreatic duct") Ampulla of Vater (60) connects to the duodenum (50) to deliver bile and pancreatic enzymes into small intestine (46) to mix with and process chyme that exits stomach (44).

As indicated by flow arrows in FIG. 2A, chyme is shown flowing through small intestine (46) along a natural flow path such that the chyme exiting stomach (44) passes directly into and flows downstream through duodenum (50), through jejunum (52), through ileum (54), and passes into the ascending portion of colon (48). FIG. 2A also shows gastrointestinal tract (40) after having undergone surgical steps of an exemplary gastric procedure. These steps include transecting stomach (44) along its length to remove a portion (45) along the greater curvature and leave a tubular-shaped pouch, similar to a sleeve gastrectomy. Additionally, a downstream portion (62) of small intestine (46) is joined with an upstream portion (64) of small intestine (46) via a side-by-side anastomosis (66). Downstream portion (62) may be a lower portion of jejunum (52) or an upper portion of ileum (54), and upstream portion (64) may be a lower portion of duodenum (50) or an upper portion of jejunum (52), for example. As shown in FIGS. 2A and 2B, anastomosis (66) is located downstream of the location at which ampulla of Vater (60) connects with small intestine (46).

The transection of stomach (44) and formation of anastomosis (66) may be performed using various suitable surgical methods and instruments readily apparent to those of ordinary skill in the art in view of the teachings herein. Furthermore, one may employ any one or more of the surgical methods and instruments described in U.S. Pat. No. 6,543,456, entitled "Method for Minimally Invasive Surgery in the Digestive System," issued Apr. 8, 2003; and/or U.S. Pat. No. 8,636,751, entitled "Methods and Devices for Rerouting of Chyme to Induce Intestinal Brake," issued Jan. 28, 2014, the disclosures of which are incorporated by reference here.

FIG. 2A also shows an artificial sphincter (126) encircling a portion of small intestine (46) at a location immediately downstream of anastomosis (66). As shown in FIGS. 2A and 2B, artificial sphincter (126) is configured to transition between an open, radially-expanded state (FIG. 2A), and a closed, radially-constricted state (FIG. 2B). Exemplary structural features of artificial sphincter (126) are described in greater detail below. FIG. 2A shows artificial sphincter (126) in the open state in which artificial sphincter (126) permits intestinal flow to pass through the encircled portion of small intestine (46) such that the intestinal flow follows a natural flow path through duodenum (50), jejunum (52), and ileum (54). FIG. 2B shows artificial sphincter (126) in the closed state in which artificial sphincter (126) radially constricts the encircled portion of small intestine (46) and thereby blocks intestinal flow from passing therethrough. As a result, the intestinal flow is redirected through anastomosis (66) such that the intestinal flow passes directly from upstream intestine portion (64) to downstream intestine portion (62), bypassing at least a portion of jejunum (52). In some instances, anastomosis (66) may be suitably located such that the intestinal flow bypasses most or all of jejunum (52) when artificial sphincter (126) is closed.

As shown in FIGS. 2A and 2B, the intestinal flow receives bile and pancreatic enzymes from ampulla of Vater (60) before passing through the encircled portion of small intestine (46) when artificial sphincter (126) is open (see FIG. 2A), or before being redirected through anastomosis (66) when artificial sphincter (126) is closed (see FIG. 2B). Accordingly, artificial sphincter (126) may be selectively transitioned between the open and closed states without altering the delivery of bile and pancreatic enzymes to the chyme.

As described in greater detail below, artificial sphincter (126) is operable to transition between the open and closed states in response to a user-activated electrical input, which may be provided by the patient or the physician, to selectively alter the flow path of chyme through small intestine (46) between a natural flow path (FIG. 2A) and a redirected flow path (FIG. 2B). This ability to selectively alter the intestinal flow path via actuation of the artificial sphincter (126) enables the patient and physician to achieve a desired anatomical response for the patient.

Figure 3:
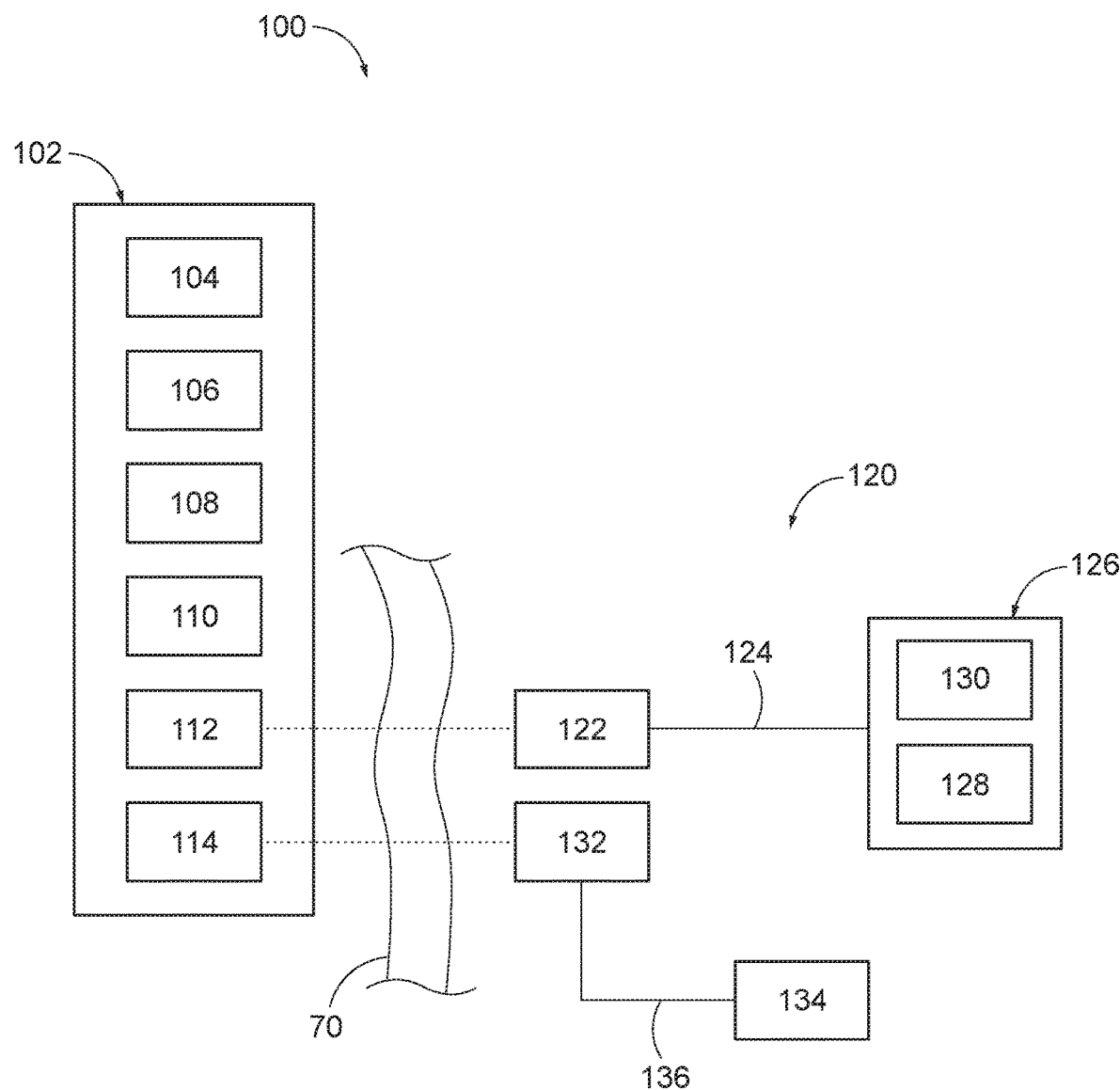
FIG. 3 depicts a schematic view of an exemplary implant device having an artificial sphincter configured to function in the manners shown in FIGS. 2A and 2B.

B. Overview of Exemplary Implant Device Having TET-Controlled Artificial Sphincter FIG. 3 shows a schematic illustration of an exemplary implant device (100) that incorporates artificial sphincter (126) shown in FIGS. 2A and 2B. Implant device (100) includes an external (or "extracorporeal") portion (102) configured to be positioned externally of a patient, and an implantable (or "intracorporeal") portion (120) configured to be implanted within the patient. As described in greater detail below, external portion (102) is configured to power implantable portion (120), including artificial sphincter (126), wirelessly via transcutaneous energy transfer (TET). While implant device (100) and the exemplary versions of its artificial sphincter (126) are shown and described herein as being used for selective constriction of small intestine (46), it will be appreciated that implant device (100) may be employed in various other medical applications for selective constriction of other anatomical structures and corresponding passages, such as esophagus (42), stomach (44), or a urethra (not shown), for example.

External portion (102) of implant device (100) is configured to be mounted to the exterior of the patient's abdomen (70) and includes a controller (104), a user input feature (106), a visual indicator (108), a power source (110), an external power-signal transmitter in the form of a primary TET coil (112), and an external sensor-signal receiver in the form of a telemetry coil (114). User input feature (106) may be in the form of one or more buttons, switches, dials, or other user-engageable features, and is configured to be activated by a user to provide an electrical input that causes implant device (100) to transition artificial sphincter (126) between the open state and the closed state, as described below. Visual indicator (108) may be in the form of one or more lights, indicia, or other visual features configured to provide a user with a visual indication of a whether artificial sphincter (126) is open or closed, among other conditions associated with the operation of artificial sphincter (126). Power source (110) of the present example is in the form of a battery enclosed within a housing of external portion (102), and may be disposable or rechargeable. As described below, external TET coil (112) is configured to wirelessly transmit transcutaneous power signals to implantable portion (120), and external telemetry coil (114) is configured to wirelessly receive transcutaneous sensor signals from implantable portion (120). External coils (112, 114) may be electrically isolated from another and provided with different resonant frequencies suitable to enable simultaneous TET and telemetry through the patient's skin.

Implantable portion (120) of implant device (100) is configured to be implanted within the patient's abdominal region using known surgical methods and instruments readily apparent to those of ordinary skill in the art in view of the teachings herein. Implantable portion (120) includes an internal power-signal receiver in the form of a secondary TET coil (122) that inductively couples with external primary TET coil (112) to receive transcutaneous transmission of power signals. In the present example, internal TET coil (122) is secured to an interior wall of the patient's abdomen (70) such that TET coils (112, 122) are within TET transmission range of one another. Internal TET coil (122) is electrically coupled to artificial sphincter (126) with a flexible wire (124). Artificial sphincter (126) of implantable portion (120) includes an actuator (128) and a constricting member (130) configured to be actuated by actuator (128) to transition artificial sphincter (126) between open and closed states. Internal TET coil (122) is configured to selectively activate actuator (128) for actuating constricting member (130) in response to receiving TET from external TET coil (112). As described below, actuator (128) and constricting member (130) may take various suitable forms.

Implantable portion (120) of the present example further includes an internal sensor-signal transmitter in the form of a second telemetry coil (132) that inductively couples with external telemetry coil (114), and which is electrically coupled to an internal sensor (134) with a second wire (136). Internal sensor (134) may be of any suitable sensor type configured to detect a condition of artificial sphincter (126)

or of one or more anatomical features affected by artificial sphincter (126). For instance, internal sensor (134) may be configured to detect a change in dimension of artificial sphincter (126) or a pressure exerted on the encircled portion of small intestine (46) as artificial sphincter (126) transitions between open and closed states. Sensor signals generated by internal sensor (134) are communicated to internal telemetry coil (132), which then transmits the sensor signals to external telemetry coil (114) transcutaneously. The received sensor signals are then analyzed by controller (104) of external portion (102), which may then direct visual indicator (108) and/or other external indicating features (not shown) to provide a user-detectable indication corresponding to the condition detected by internal sensor (134). By way of example only, visual indicator (108) may comprise one or more light emitting diodes (LEDs) configured to visually indicate that artificial sphincter (126) is in the process of assuming or has fully assumed a closed or open state that effects a transition of the intestinal flow path as described above. It will be appreciated that telemetry coils (114, 132) and internal sensor (134) are merely optional and may be omitted in some versions. In such versions, visual indicator (108) may be configured to provide a visual indication automatically in response to actuation of user input feature (106), rather than in response to sensor signals received from internal sensor (134).

The TET and telemetry components of external and implantable portions (102, 120) of implant device (100) may be further configured and operable in accordance with any one or more teachings of the references incorporated by reference herein, such as U.S. Pat. No. 8,870,742, entitled "GUI for an Implantable Restriction Device and a Data Logger," and U.S. Pat. No. 7,390,294, entitled "Piezo Electrically Driven Bellows Infuser for Hydraulically Controlling an Adjustable Gastric Band."

Figure 4:
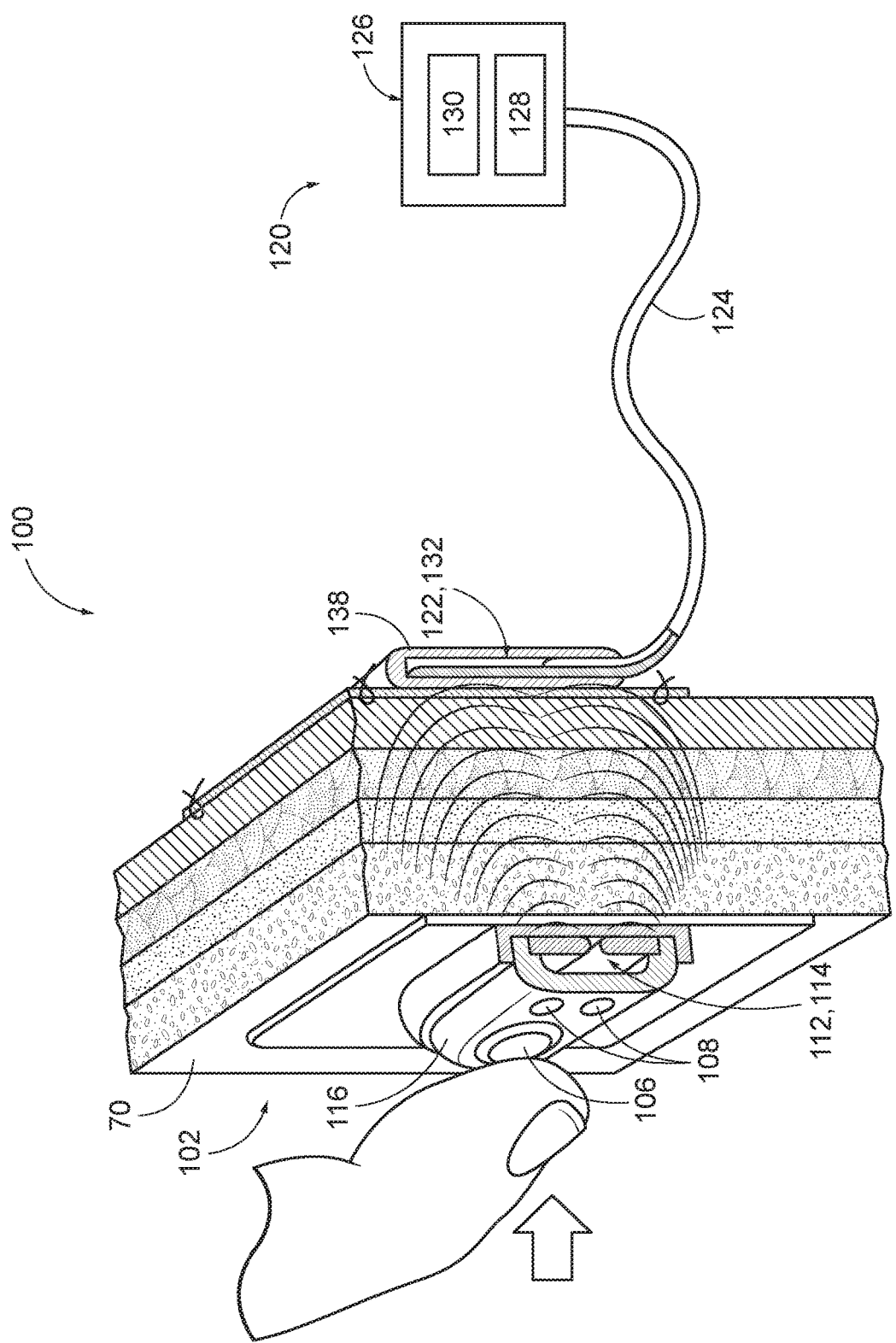
FIG. 4 depicts a schematic perspective view of an exemplary external portion of the implant device of FIG. 3.

FIG. 4 shows an exemplary configuration of external portion (102) and implantable portion (120) of implant device (100). External portion (102) is affixed to an exterior surface of the patient's abdomen (70) and includes an external housing (116) that supports a user input feature (106) in the form of a button, and a visual indicator (108) in the form of a pair of LEDs. External housing (116) encloses controller (104), battery (110), external TET coil (112), and external telemetry coil (114). Implantable portion (120) includes an internal housing (138) that encloses internal TET coil (122) and internal telemetry coil (132), and which is affixed to an interior surface of abdomen (70) such that internal coils (122, 132) are positioned within transcutaneous transmitting range of the respective external coil (112, 114). As shown, user input button (106) is configured to be depressed momentarily to activate external TET coil (112) to transmit electrical power to internal TET coil (122), which then activates actuator (128) of artificial sphincter (126) to actuate constricting member (130) to transition artificial sphincter (126) between the open and closed states, thereby altering the intestinal flow path within the patient.

C. Exemplary Artificial Sphincter Having Electromagnetic Actuator

Figure 5A:
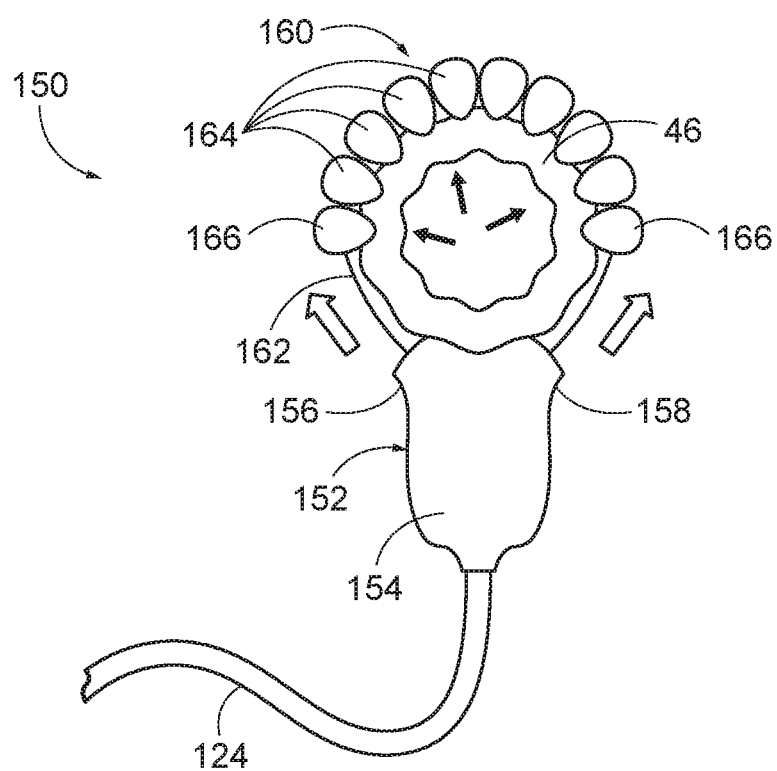
FIG. 5A depicts a schematic front elevational view of an exemplary version of the artificial sphincter of the implant device of FIG. 3, showing the artificial sphincter encircling a portion of the small intestine and in an open state that permits intestinal flow through the encircled portion, with the small intestine being shown in cross-section.
Figure 5B:
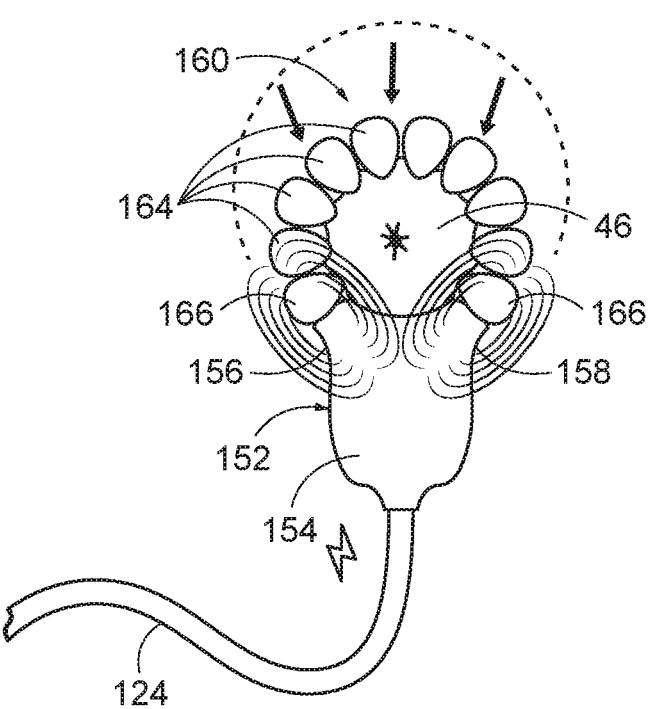
FIG. 5B depicts a schematic front elevational view of the exemplary artificial sphincter of FIG. 5A, showing the artificial sphincter in a closed state that blocks intestinal flow through the encircled portion, with the small intestine being shown in cross-section.

FIGS. 5A and 5B show an exemplary version of artificial sphincter (126) of implant device (100), in the form of artificial sphincter (150). Artificial sphincter (150) includes an actuator (152) that comprises an electromagnet (154) enclosed within a housing having a first lug feature (156) and a second lug feature (158) arranged adjacent to one another at an operating end of actuator (152). Artificial sphincter (150) further includes a constricting member (160) that comprises a flexible elongate member (162) having a first end slidably received by first lug feature (156) and a second end slidably received by second lug feature (158). Flexible elongate member (162) may be in the form of a metal wire or a thread formed of various biocompatible materials. Constricting member (160) further includes a plurality of beads (164) coupled to and spaced along an exposed length of flexible elongate member (162), and a pair of magnetic elements (166) affixed to flexible elongate member (162) at respective first and second opposed ends of beads (164). Beads (164) may be slidable along the portion of flexible elongate member (162) extending between magnetic elements (166). Magnetic elements (166) may be shaped similar to beads (164), and may comprise a magnetic material, such as a ferrous metal. In some versions, magnetic elements (166) may be permanent magnets. While constricting member (130) of the present version is shown having eight beads (164) and two magnetic elements (166), it will be appreciated that various alternative quantities and arrangements of beads (164) and magnetic elements (166) may be provided in other versions.

As shown in FIGS. 5A and 5B, actuator (152) and constricting member (160) define a generally annular shape having a circular central opening configured to receive a portion of small intestine (46), or another anatomical structure to be constricted, therethrough. In the present version, actuator (128) includes a concave portion between first and second lug features (156, 158) that is configured to mate with the outer curvature of small intestine (46) to provide more effective constriction. As shown, flexible elongate member (162), beads (164), and magnetic elements (166) are configured to extend about and bear radially inwardly against a first circumferential portion of small intestine (46), and the operating end of actuator (128) is configured to extend about and bear radially inwardly against an opposed second circumferential portion of small intestine (46). During implantation of implantable portion (120), one of the ends of flexible elongate member (162) may be released from actuator (152) and directed circumferentially around small intestine (46) before being recoupled with actuator (152).

As shown in FIGS. 5A and 5B, electromagnet (154) of the present example may be selectively activated and deactivated to transition artificial sphincter (150) between open and closed states. FIG. 5A shows artificial sphincter (150) in a radially-expanded open state when electromagnet (154) is deactivated. In this state, magnetic elements (166) of constricting member (160) are not magnetically biased toward lug features (156, 158), thereby enabling constricting member (160) to assume an enlarged effective circumference that permits the encircled portion of small intestine (46) to assume its natural expanded shape so that intestinal flow may pass therethrough.

FIG. 5B shows artificial sphincter (150) in a radially-contracted closed state when electromagnet (154) is activated. In this activated state, magnetic elements (166) are drawn magnetically toward the respective lug features (156, 158) of actuator (152), thereby reducing an active length and thus an effective circumference of constricting member (160), such that artificial sphincter (150) contracts radially. In particular, beads (164), magnetic elements (166), and lug features (156, 158) collectively clamp inwardly against and constrict the encircled portion of small intestine (46) sufficiently to block intestinal flow therethrough. As a result, the intestinal flow is redirected along an alternate flow path, as described above in connection with FIGS. 2A and 2B.

In some versions, implant device (100) may be configured to limit a magnetic attraction force exerted between electromagnet (154) and magnetic elements (166) to a predetermined threshold. Such force threshold may be selected to be high enough to effectively constrict the encircled portion of small intestine (46) to block intestinal flow therethrough, yet low enough to avoid over-constriction and resultant damage to the intestinal tissue. Implant device (100) may be configured to monitor a pressure exerted by artificial sphincter (150) on small intestine (46) as a result of the magnetic attraction force between magnetic components (154, 166), and to provide an alert to the patient when a pressure threshold is approached and/or exceeded. Such monitoring may be performed via internal sensor (134), for example.

In the present example, electromagnet (154) of artificial sphincter (150) is configured to transition between an activated state and a deactivated state in response to actuation of user input feature (106). During implantation of implant device (100), electromagnet (154) may be placed in a deactivated state. Following implantation, the patient, physician, or other user may actuate user input feature (106) to cause external TET coil (112) to transmit electrical power signals to internal TET coil (122), which then activates electromagnet (154) to thereby close artificial sphincter (150) and constrict the encircled portion of small intestine (46). Once activated, external TET coil (112) maintains TET such that electromagnet (154) remains in an activated state to thereby maintain closure of artificial sphincter (150) and constriction of small intestine (46). In response to a subsequent activation of user input feature (106), external TET coil (112) ceases TET to thereby deactivate electromagnet (154) and permit artificial sphincter (126) to return to an open state via natural expansion forces exerted by the encircled portion of small intestine (46). Each subsequent actuation of user input feature (106) operates to transition electromagnet (154) between activated and deactivated states to effect closure and opening of artificial sphincter (150). As described above, visual indicator (108) of external portion (102) is configured to inform an observer of the current state of artificial sphincter (150).

In some versions, for instance where magnetic elements comprise permanent magnets, electromagnet (154) may remain in a constantly-activated state following implantation rather than being selectively activated and deactivated. In such versions, actuation of user input feature (106) may operate to reverse the polarity of electromagnet (154) to thereby attract or repel magnetic elements (166) to transition artificial sphincter (150) between the open and closed states.

D. Exemplary Artificial Sphincter Having Motorized Actuator

Figure 6:
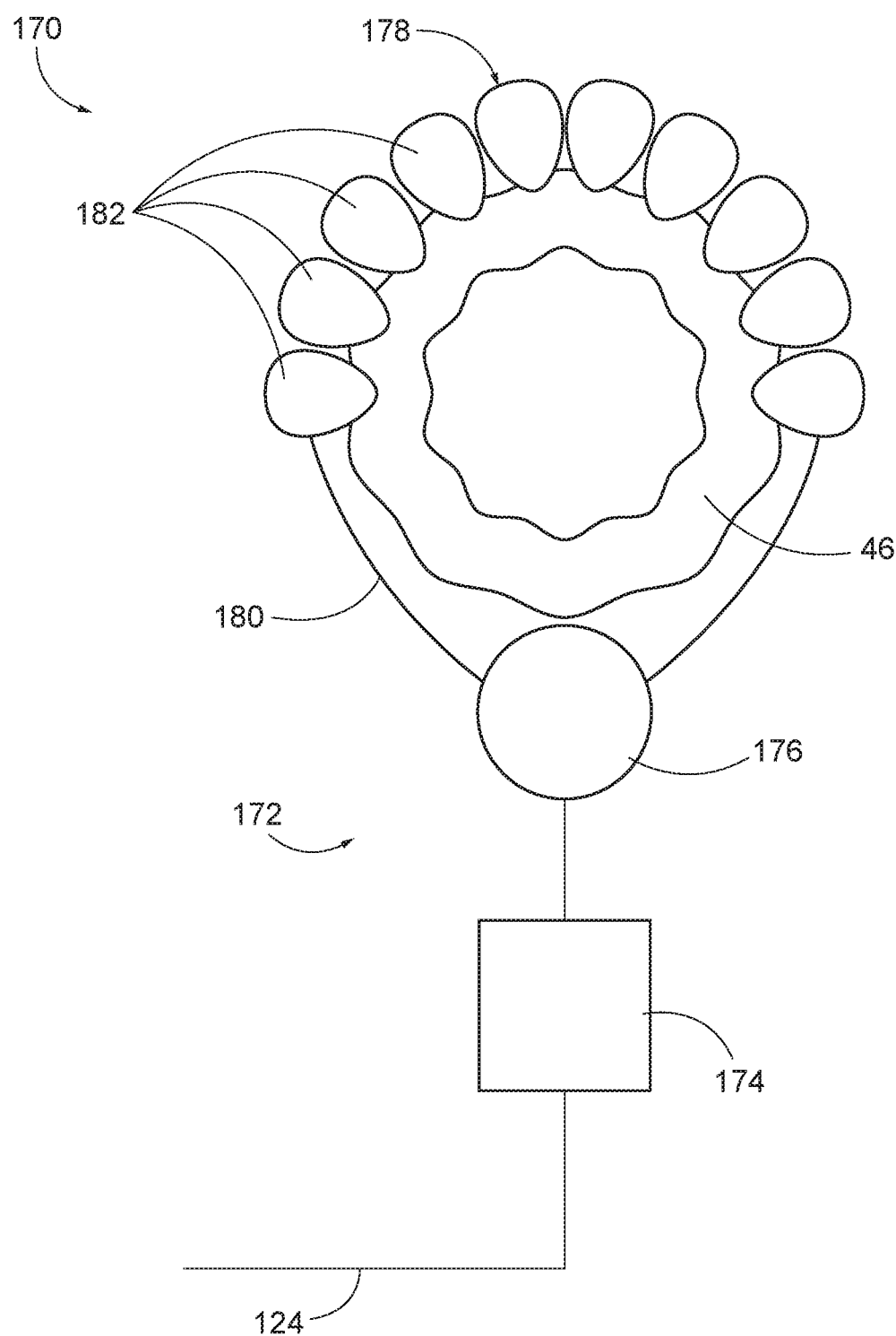
FIG. 6 depicts schematic front view of another exemplary version of the artificial sphincter of FIG. 3.

FIG. 6 shows another exemplary version of artificial sphincter (126) of implant assembly (100), in the form of artificial sphincter (170). Artificial sphincter (170) includes an actuator (172) that comprises a motor (174) and a spool (176) configured to be rotatably driven by motor (174). Constricting member (178) comprises a flexible elongate member (180) having first and second ends retractably coupled with spool (176), and a plurality of beads (182) spaced along an active portion of flexible elongate member (180). Flexible elongate member (180) and beads (182) may be similar to flexible elongate member (162) and beads (164) described above. Moreover, artificial sphincter (170) is configured in a manner similar to artificial sphincter (150) such that constricting member (178) extends about and bears radially inwardly against a first circumferential side of small intestine (46), and spool (176) bears radially inwardly against an opposed second circumferential side of small intestine (46).

In use, motor (174) is operable to rotate spool (176) in first and second directions to retract and extend flexible elongate member (180), respectively, to transition artificial sphincter (170) between respective open and closed states. FIG. 6 shows artificial sphincter (170) in an open, radially-expanded state in which constricting member (178) is provided with an enlarged effective circumference that permits the encircled portion of small intestine (46) to assume its natural expanded shape so that intestinal flow may pass therethrough. Motor (174) may then be activated to rotate spool (176) in a first direction to retract flexible elongate member (180) and thereby contract constricting member (178) about small intestine (46). As described above in connection with constricting member (160) and FIG. 5B, this contraction of constricting member (178) radially constricts small intestine (46) to block intestinal flow therethrough. Subsequently, motor (174) may be activated to rotate spool (176) in an opposite second direction to extend flexible elongate member (180) and thereby permit artificial sphincter (170) to return to the radially-expanded open state shown in FIG. 6.

Motor (174) may be activated to rotate in one direction or the other in response to power received from internal TET coil (122) based on TET received from external TET coil (112) in response to actuation of user input feature (106). For instance, a first actuation of user input feature (106) following implantation of implant device (100) may initiate TET that directs motor (174) to rotate spool (176) in the first direction to close artificial sphincter (170). Each subsequent activation of user input feature (106) may initiate TET that directs motor (174) to rotate spool (176) in successively alternating directions to thereby transition artificial sphincter (170) between the closed and open states. A present state of artificial sphincter (170) may be indicated visually to an observer via visual indicator (108) of external portion (102) of implant device (100).

Controller (104) of external portion (102) may be operable to ensure that motor (174) rotates spool (176) in each direction by a predetermined amount corresponding to the open and closed states of artificial sphincter (170). For example, controller (104) may be configured to determine that artificial sphincter (170) has reached the closed state or the open state based on signals received from internal sensor (134), via telemetry coils (114, 132). In another example, implantable portion (120) may include an encoder (not shown) configured to provide signals to controller (104), via telemetry coils (114, 132), corresponding to a rotational state of motor (174) or spool (176). In response to receiving such signals from internal sensor (134) or an encoder, controller (104) may determine that the transition of artificial sphincter (170) is complete and then deactivate motor (174) to maintain the current state of artificial sphincter (170).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of rerouting flow through the small intestine of a patient with an implanted artificial sphincter that encircles a portion of the small intestine, wherein the small intestine includes a duodenum, a jejunum extending from the duodenum, and an ileum extending from the jejunum, the method comprising: (a) providing the artificial sphincter in an open state to thereby permit intestinal flow through the encircled portion of the small intestine such that the intestinal flow passes through the duodenum, the jejunum, and the ileum; and (b) in response to a user-activated electrical input, transitioning the artificial sphincter to a closed state to constrict the encircled portion of the small intestine and thereby redirect intestinal flow from a first portion of the small intestine to a second portion of the small intestine such that the intestinal flow bypasses at least a portion of the jejunum.

Example 2

The method of Example 1, further comprising, in response to a second user-activated electrical input, transitioning the artificial sphincter from the closed state to the open state.

Example 3

The method of any of the preceding Examples, wherein the artificial sphincter is located downstream of an anastomosis formed between the first portion of the small intestine and the second portion of the small intestine, wherein in the closed state the artificial sphincter redirects intestinal flow from the first portion directly to the second portion via the anastomosis.

Example 4

The method of any of the preceding Examples, wherein the artificial sphincter is located downstream of a location at which an ampulla of Vater connects with the small intestine.

Example 5

The method of any of the preceding Examples, wherein the artificial sphincter comprises an actuator and a constricting member coupled with the actuator, wherein transitioning the artificial sphincter to the closed state comprises actuating the constricting member with the actuator to constrict the encircled portion of the small intestine.

Example 6

The method of Example 5, wherein transitioning the artificial sphincter to the closed state comprises reducing an effective circumference of the artificial sphincter by shortening an active length of the constricting member.

Example 7

The method of any of Examples 5 through 6, wherein the actuator is positioned on a first side of the small intestine and the constricting member extends circumferentially around an opposed second side of the small intestine.

Example 8

The method of any of Examples 5 through 7, wherein the constricting member comprises a flexible elongate member.

Example 9

The method of any of Examples 5 through 8, wherein the constricting member comprises a plurality of bodies, wherein transitioning the artificial sphincter from the open state to the closed state comprises drawing the bodies toward the actuator.

Example 10

The method of any of Examples 5 through 9, wherein the constricting member comprises a magnetic element.

Example 11

The method of Example 10, wherein the actuator comprises an electromagnet, wherein transitioning the artificial sphincter from the open state to the closed state comprises activating the electromagnet to attract the magnetic element.

Example 12

The method of Example 11, further comprising, in response to a second user-activated electrical input, deactivating the electromagnet to permit the artificial sphincter to return to the open state Example 13

The method of any of the preceding Examples, wherein the artificial sphincter is operatively coupled with a power source provided externally of the patient, wherein transitioning the artificial sphincter from the open state to the closed state comprises transmitting electrical power from the power source to the artificial sphincter wirelessly.

Example 14

The method of any of the preceding Examples, wherein the artificial sphincter is coupled with an internal coil implanted within the patient, wherein the internal coil is inductively coupled with an external coil provided externally of the patient, wherein transitioning the artificial sphincter from the open state to the closed state comprises transmitting electrical power from the external coil to the internal coil via transcutaneous energy transfer (TET).

Example 15

The method of Example 14, wherein the TET is activated in response to actuation of an external user input feature that provides the electrical input.

Example 16

A method of rerouting flow through the small intestine of a patient, wherein the small intestine includes a duodenum, a jejunum extending from the duodenum, and an ileum extending from the jejunum, the method comprising: (a)

forming an anastomosis between a first portion of the small intestine and a second portion of the small intestine; and (b) positioning an artificial sphincter about the small intestine at a location downstream of the anastomosis, wherein in response to a user-activated electrical input the artificial sphincter is configured to transition between: (i) an open state in which the artificial sphincter permits intestinal flow to pass through the duodenum, the jejunum, and the ileum, and (ii) a closed state in which the artificial sphincter redirects intestinal flow from the first portion of the small intestine directly to the second portion, via the anastomosis, such that the intestinal flow bypasses at least a portion of the jejunum.

Example 17

The method of Example 16, wherein forming the anastomosis in the small intestine comprises forming the anastomosis downstream of a location at which an ampulla of Vater connects with the small intestine.

Example 18

An apparatus comprising: (a) an extracorporeal portion configured to be arranged externally of a patient, wherein the extracorporeal portion comprises: (i) a user input feature, (ii) a power source operatively coupled with the user input feature, and (iii) a transmitter electrically coupled with the power source; and (b) an intracorporeal portion configured to be implanted within the patient, wherein the intracorporeal portion comprises: (i) a receiver in wireless communication with the transmitter, and (ii) an artificial sphincter electrically coupled with the receiver, wherein the artificial sphincter is sized to encircle a portion of the small intestine of the patient, wherein the artificial sphincter comprises: (A) an actuator having an electromagnet, and (B) a magnetic constricting member operatively coupled with the actuator, wherein the magnetic constricting member is configured to bear against the encircled portion of the small intestine, wherein the receiver is configured to receive electrical power from the transmitter via transcutaneous energy transfer in response to actuation of the user input feature, wherein the receiver is configured to activate the electromagnet to attract the magnetic constricting member and thereby contract the artificial sphincter to constrict the encircled portion of the small intestine.

Example 19

The apparatus of Example 18, wherein the transmitter comprises a transmitting coil, wherein the receiver comprises a receiving coil inductively coupled with the transmitting coil.

Example 20

The apparatus of any of Examples 18 through 19, wherein the magnetic constricting member includes at least one permanent magnet.

III. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of rerouting flow through the small intestine of a patient with an implanted artificial sphincter that encircles a portion of the small intestine, wherein the small intestine includes a duodenum, a jejunum extending from the duodenum, and an ileum extending from the jejunum, the method comprising:
   (a) providing the artificial sphincter in an open state to thereby permit intestinal flow through the encircled portion of the small intestine such that the intestinal flow passes through the duodenum, the jejunum, and the ileum; and
   (b) in response to a first user-activated electrical input, transitioning the artificial sphincter to a closed state to constrict the encircled portion of the small intestine and thereby redirect intestinal flow from a first portion of the small intestine to a second portion of the small intestine such that the intestinal flow bypasses at least a portion of the jejunum,
   wherein the artificial sphincter comprises an actuator and a constricting member coupled with the actuator, wherein transitioning the artificial sphincter to the closed state comprises actuating the constricting member with the actuator to constrict the encircled portion of the small intestine.

2. The method of claim 1, further comprising, in response to a subsequent user-activated electrical input, transitioning the artificial sphincter from the closed state to the open state.

3. The method of claim 1, wherein the artificial sphincter is located downstream of an anastomosis formed between the first portion of the small intestine and the second portion of the small intestine, wherein in the closed state the artificial sphincter redirects intestinal flow from the first portion directly to the second portion via the anastomosis.

4. The method of claim 1, wherein the artificial sphincter is located downstream of a location at which an ampulla of Vater connects with the small intestine.

5. The method of claim 1, wherein transitioning the artificial sphincter to the closed state comprises reducing an effective circumference of the artificial sphincter by shortening an active length of the constricting member.

6. The method of claim 1, wherein the actuator is positioned on a first side of the small intestine and the constricting member extends circumferentially around an opposed second side of the small intestine.

7. The method of claim 1, wherein the constricting member comprises a flexible elongate member.

8. The method of claim 1, wherein the constricting member comprises a plurality of bodies, wherein transitioning the artificial sphincter from the open state to the closed state comprises drawing the bodies toward the actuator.

9. The method of claim 1, wherein the constricting member comprises a magnetic element.

10. The method of claim 9, wherein the actuator comprises an electromagnet, wherein transitioning the artificial sphincter from the open state to the closed state comprises activating the electromagnet to attract the magnetic element.

11. The method of claim 10, further comprising, in response to a subsequent user-activated electrical input, deactivating the electromagnet to permit the artificial sphincter to return to the open state.

12. The method of claim 1, wherein the artificial sphincter is operatively coupled with a power source provided externally of the patient, wherein transitioning the artificial sphincter from the open state to the closed state comprises transmitting electrical power from the power source to the artificial sphincter wirelessly.

13. The method of claim 1, wherein the artificial sphincter is coupled with an internal coil implanted within the patient, wherein the internal coil is inductively coupled with an external coil provided externally of the patient, wherein transitioning the artificial sphincter from the open state to the closed state comprises transmitting electrical power from the external coil to the internal coil via transcutaneous energy transfer (TET).

14. The method of claim 13, wherein the TET is activated in response to actuation of an external user input feature that provides the first user-activated electrical input.

15. A method of rerouting flow through the small intestine of a patient, wherein the small intestine includes a duodenum, a jejunum extending from the duodenum, and an ileum extending from the jejunum, the method comprising:
   (a) forming an anastomosis between a first portion of the small intestine and a second portion of the small intestine; and
   (b) positioning an artificial sphincter about the small intestine at a location downstream of the anastomosis, wherein in response to a user-activated electrical input the artificial sphincter is configured to transition between:
     (i) an open state in which the artificial sphincter permits intestinal flow to pass through the duodenum, the jejunum, and the ileum, and
     (ii) a closed state in which the artificial sphincter redirects intestinal flow from the first portion of the small intestine directly to the second portion, via the anastomosis, such that the intestinal flow bypasses at least a portion of the jejunum.

16. The method of claim 15, wherein forming the anastomosis in the small intestine comprises forming the anastomosis downstream of a location at which an ampulla of Vater connects with the small intestine.

17. A method of rerouting flow through an anatomical structure of a patient with an implanted artificial sphincter that encircles a portion of the anatomical structure, wherein the anatomical structure includes an upstream passage, an intermediate passage extending from the upstream passage, and a downstream passage extending from the intermediate passage, the method comprising:
   (a) providing the artificial sphincter in an open state to thereby permit fluid flow through the encircled portion of the anatomical structure such that the fluid flow passes through the upstream passage, the intermediate passage, and the downstream passage; and
   (b) in response to a first user-activated electrical input, transitioning the artificial sphincter to a closed state to constrict the encircled portion of the anatomical structure and thereby redirect fluid flow from the upstream passage to the downstream passage such that the fluid flow bypasses the intermediate passage,
   wherein the artificial sphincter comprises an actuator and a constricting member coupled with the actuator, wherein transitioning the artificial sphincter to the closed state comprises actuating the constricting member with the actuator to constrict the encircled portion of the anatomical structure.

18. The method of claim 17, further comprising, in response to a subsequent user-activated electrical input, transitioning the artificial sphincter from the closed state to the open state.

19. The method of claim 17, wherein the artificial sphincter is located downstream of an anastomosis formed between the upstream passage and the downstream passage, wherein in the closed state the artificial sphincter redirects fluid flow from the upstream passage directly to the downstream passage via the anastomosis.

20. The method of claim 17, wherein transitioning the artificial sphincter to the closed state comprises reducing an effective circumference of the artificial sphincter by shortening an active length of the constricting member.

* * * * *